(12) United States Patent
Chang et al.

(10) Patent No.: US 7,964,721 B2
(45) Date of Patent: Jun. 21, 2011

(54) RATIOMETRIC FLUORESCENT CHEMOSENSOR FOR SELECTIVE DETECTION OF HG (II) IONS

(75) Inventors: Suk-Kyu Chang, Gwacheon-si (KR); Jun Soo Kim, Seoul (KR); Myung Gil Choi, Gwangju-si (KR); Ki Cheol Song, Incheon (KR); Sangdoo Ahn, Seoul (KR); Kyoung Tai No, Seoul (KR)

(73) Assignee: Chung-Ang University Industry-Academy Cooperation Foundation, Seoul (KR)

( * ) Notice: Subject to any disclaimer, the term of this patent is extended or adjusted under 35 U.S.C. 154(b) by 700 days.

(21) Appl. No.: 11/973,522

(22) Filed: Oct. 9, 2007

(65) Prior Publication Data

US 2008/0255346 A1  Oct. 16, 2008

(30) Foreign Application Priority Data

Apr. 11, 2007 (KR) ........................ 10-2007-0035639

(51) Int. Cl.
*C07D 273/00* (2006.01)
(52) U.S. Cl. ...................................... 540/467
(58) Field of Classification Search ........................ None
See application file for complete search history.

(56) References Cited

U.S. PATENT DOCUMENTS 7,615,377 B2 * 11/2009 Lippard et al. ............... 436/166
2005/0112769 A1  5/2005 Lippard et al.

OTHER PUBLICATIONS

Kim et al. Organic Letters, 2007, 9(6), 1129-32.*
Kim et al. Tetrahedron Letters, 2006, 47, 497-500.*
Caballero, et al., "Highly Selective Chromogenic and Redox or Fluorescent Sensors of $Hg^{2+}$ in Aqueous Environment Based on 1,4-Disubstituted Azines;" *J. Am. Chem. Soc.* (2005); vol. 127, 15666-15667.
Song, et al.; "Fluorogenic Hg2+—Selective Chemodosimeter Derived from 8-Hydroxyquinoline;" *Organic Letters*; (2006); vol. 8, No. 16, 3413-3416.
Takahashi, Y.; Kasai, H.; Nakanishi, H.; Suzuki, T. M. Angew; *Chem., Int. Ed.* 2006, 45, 913.
Oehme, I.; Wolfbeis, O. S.; *Mikrochim. Acta* 1997, 126, 177.
Bonfil, Y.; Brand, M.; Kirowa-Eisner; E. *Anal. Chim. Acta* 2002, 464, 99.
Kollmannsberger, M.; Rurack, K.; Resch-Genger, U; Rettig, W; Daub J *Chem. Phys. Lett.* 2000, 329, 363.
Rurack, K; Sczepan, M.; Spieles, M.; Resch-Genger, U.; Rettig; W. *Chem. Phys. Lett.* 2000, 320, 87.
Dujols, V.; Ford, F.; Czarnik, A. W.; *J. Am. Chem. Soc.* 1997, 119, 7386.
Elizabeth M. Nolan, Stephen J. Lippard;. *J. Materials. Chemistry.* 2005, 15, 2778.

* cited by examiner

*Primary Examiner* — Noble Jarrell
(74) *Attorney, Agent, or Firm* — D. Peter Hochberg; Sean F. Mellino; Daniel J. Smola

(57) ABSTRACT

A mercury selective fluorescent chemosensor for detecting mercury ions by a compound represented by formula 1 and a novel fluorescent sensitive compound prepared by introducing two aminopyrene functions as a fluorescent sensitive moiety into a binding site of the compound of formula 1 is used for selectively detecting mercury ions are provided. The mercury selective fluorescent sensitive chemosensor is a switch type chemosensor having ON-OFF-type $Hg^{2+}$-selective fluorescence quenching behavior and is not affected by other coexistent metal ions. Changes in fluorescence of the compounds of formula 1 were analyzed by ratiometric approach using monomer and excimer emissions of the pyrene fluorophore to selectively signal the concentration of mercury ions. The chemosensor can detect mercury ions in a micromolar unit even in a solution including an excess of water. Accordingly, the mercury selective fluorescent chemosensor for detecting mercury ions can be used effectively in environmental and medical applications.

12 Claims, 6 Drawing Sheets

US 7,964,721 B2

RATIOMETRIC FLUORESCENT CHEMOSENSOR FOR SELECTIVE DETECTION OF HG (II) IONS

CROSS-REFERENCE TO RELATED APPLICATIONS

This application claims foreign priority based on Korean Patent Application Serial No. 2007-35639, filed on Apr. 11, 2007, the content of which is incorporated herein by reference in its entirety.

BACKGROUND OF THE INVENTION

1. Field of the Invention

The present invention relates to a mercury selective fluorescent chemosensor for selectively detecting mercury ions ($Hg^{2+}$) by the compound represented by the formula 1. More specifically, the present invention provides a novel fluorescent sensitive compound prepared by introducing two aminopyrene subunits as a fluorescent sensitive moiety into a binding site of the compound represented by the formula 1, and provides a mercury selective fluorescent sensitive chemosensor for selectively detecting mercury ions ($Hg^{2+}$).

2. Background of the Prior Art

To develop a selective and sensitive chemosensor for the chemically or physiologically significant ionic substances, various studies have been carried out.

As an example of such studies, a method for observing optical and electrochemical chemosensing characteristics for heavy metal ions such as lead($Pb^{2+}$) and cadmium($Cd^{2+}$) ((a) Takahashi, Y.; Kasai, H.; Nakanishi, H.; Suzuki, T. M. Angew. Chem., Int. Ed. 2006, 45, 913., (b) Oehme, I.; Wolfbeis, O. S. Mikrochim. Acta 1997, 126, 177, (c) Bonfil, Y.; Brand, M.; Kirowa-Eisner, E. Anal. Chim. Acta 2002, 464, 99) is known in the art. Also, a study using selective fluorescent chemosensing characteristics for alkali metal ions and alkaline earth metal ions ((a) Kollmannsberger, M.; Rurack, K.; Resch-Genger, U; Rettig, W; Daub, J. Chem. Phys. Lett. 2000, 329, 363. (b) Rurack, K; Sczepan, M.; Spieles, M.; Resch-Genger, U.; Rettig, W. Chem. Phys. Lett. 2000, 320, 87) and a study using selective fluorescent chemosensing characteristics for copper ion ($Cu^{2+}$) (Dujols, V.; Ford, F.; Czarnik, A. W. J. Am. Chem. Soc. 1997, 119, 7386) were reported in the art.

In particular, mercury ions are well known for their toxicity in environmental field, and accordingly a research and development of detection sensor which is selective and sensitive for mercury ions ($Hg^{2+}$) has been proceeded persistently. As an example, a method for detecting mercury ions ($Hg^{2+}$) by observing selective fluorescence change with ratiometry method (Elizabeth M. Nolan, Stephen J. Lippard. J. Materials. Chemistry. 2005, 15, 2778) is known in the art. However, although it was reported that the method has selectivity for mercury ions ($Hg^{2+}$), there are the following disadvantages: the method exhibits only weak ratiometry behavior of about four-fold, the method of preparing the compound is very complicated, and the method is severely affected by nickel and copper ions.

Accordingly, the prior chemosensor having selective fluorescent sensitive characteristics for mercury ions ($Hg^{2+}$) should satisfy the following conditions: firstly, the chemosensor should not be affected by other metals in comparing with a target metal; second, the chemosensor should be able to respond even at a sufficiently low concentration; and third, the chemosensor should work even in a solution containing high water composition.

We have been persistently studying to develop a chemosensor having selective fluorescent signaling characteristics for mercury ions ($Hg^{2+}$). As a result, we produced a novel fluorescent sensitive compound by introducing two aminopyrene functions as a fluorescence sensitive moiety into a binding site of the compounds represented by the formula 1. The changes in fluorescence of the compounds represented by the formula 1 were analyzed by ratiometric approach using monomer and excimer emissions of the pyrene fluorophore to selectively signal the concentration of mercury ions ($Hg^{2+}$). In the case of detection of mercury ions ($Hg^{2+}$) with the fluorescent sensitive compound of the present invention, a mercury selective fluorescent chemosensor provided by the present invention is not affected by other metal ions; is sensitive at a lower concentration; and can detect mercury ions in micromolar concentration even in a solution including an excess of water.

SUMMARY OF THE INVENTION

Accordingly, the present invention has been made in view of the above-mentioned problems occurring in the prior art, and it is an object of the present invention to provide a mercury selective fluorescent chemosensor for selectively detecting mercury ions ($Hg^{2+}$) by the compounds represented by the formula 1.

It is another object of the present invention to provide the fluorescent sensitive compounds represented by the formula 1 and a preparation method thereof.

To accomplish the above objects, the present invention provides a mercury selective fluorescent chemosensor for selectively detecting mercury ions ($Hg^{2+}$) by the compounds represented by the formula 1.

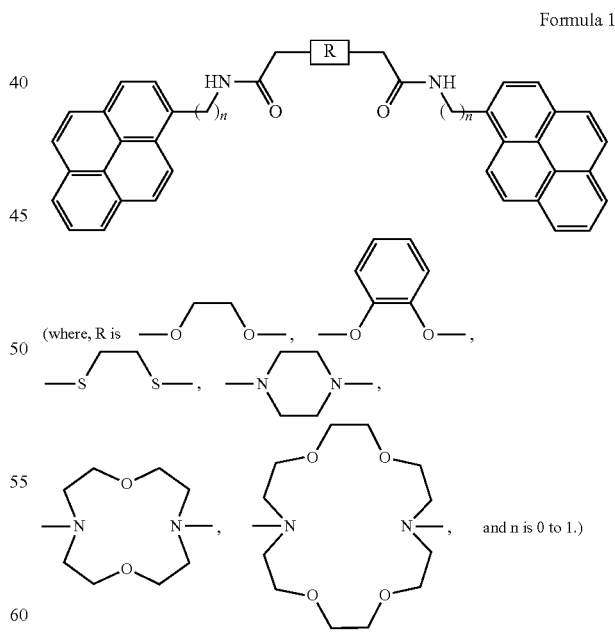

Formula 1

The mercury selective fluorescent sensitive chemosensing of the present invention is carried out by Scheme 1, that is, the chemosensor behavior is accomplished by a fluorescence change resulting from complex formation between the compound represented by the formula 1 and mercury ions ($Hg^{2+}$).

Scheme 1

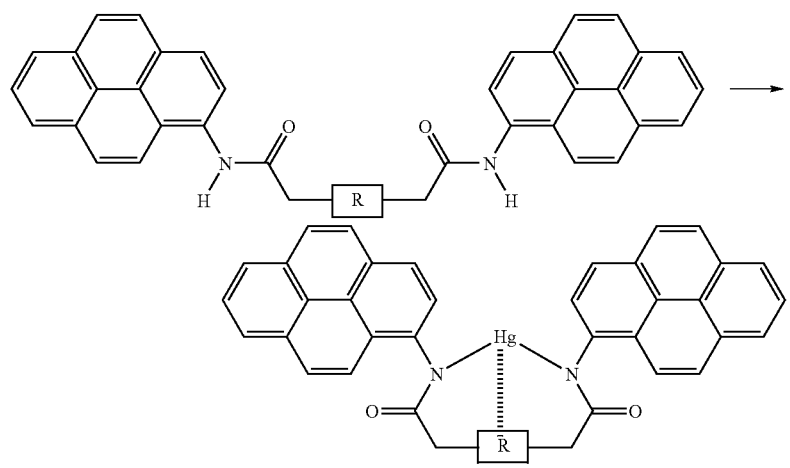

(where, R is the same as defined above.)

The mercury selective fluorescent sensitive chemosensor of the present invention shows a mercury ion (Hg$^{2+}$) selective ON-OFF-type signaling behavior under a volume ratio condition of which a mixing ratio of methanol:water is 1:1 to 2. Also, the mercury selective fluorescent sensitive chemosensor of the present invention can detect mercury ions (Hg$^{2+}$) in micromolar unit even under a condition including an excess of water.

The changes in fluorescence of the compounds represented by formula 1 were analyzed by ratiometric approach using monomer and excimer emissions of the pyrene fluorophore to selectively signal the concentration of mercury ions (Hg$^{2+}$).

An example of a compound represented by the formula 1, which is used in the mercury selective fluorescent sensitive chemosensor of the present invention, is a pyrene compound of 3,6-dioxaoctanediamide represented by the formula 2 or a methylpyrene compound of 3,6-dioxaoctanediamide represented by the formula 3. Also, the present invention provides fluorescent sensitive compounds represented by the formula 1.

Formula 1

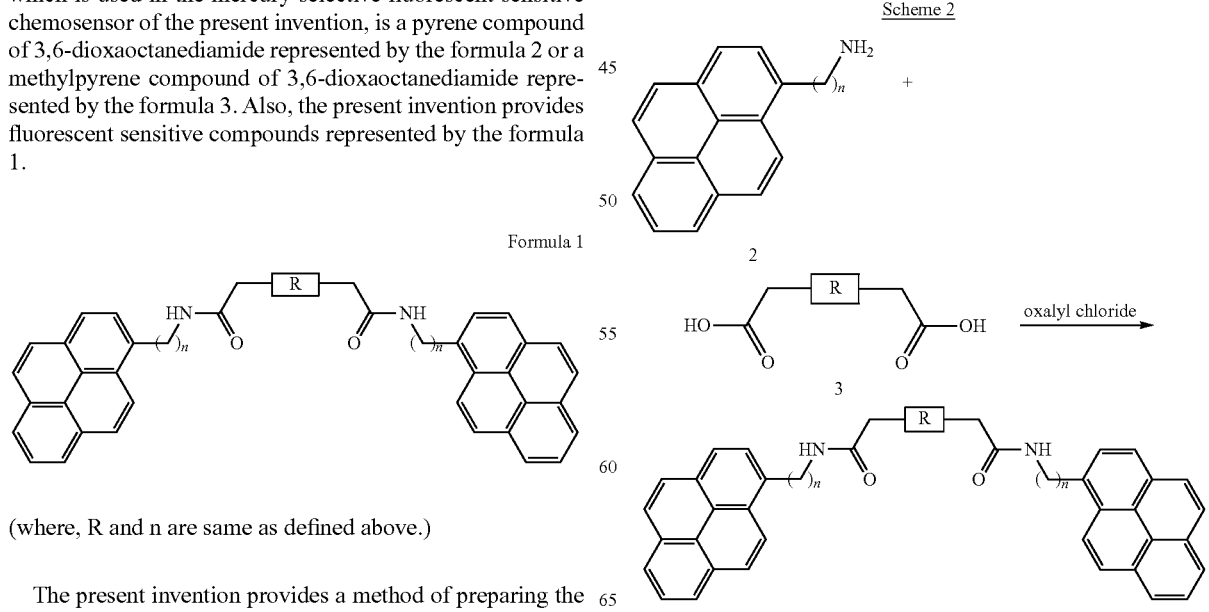

(where, R and n are same as defined above.)

The present invention provides a method of preparing the fluorescent sensitive compound, which is carried out according to the following scheme 2 when R is

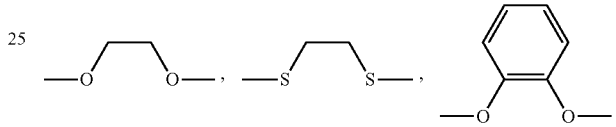

and n is 0 to 1. More specifically, the method for preparation comprises the following steps:

(1) adding dicarboxylic acid (3) into an organic solution containing oxalyl chloride ((COCl)$_2$) to prepare a reaction solution; and (2) adding an organic solution in which an aminopyrene compound (2) is contained at an equivalent ratio of 2.2 to 2.5 relative to the dicarboxylic acid (3), into the reaction solution and then reacting the resultant solution at an ambient temperature.

Scheme 2

(where, R is 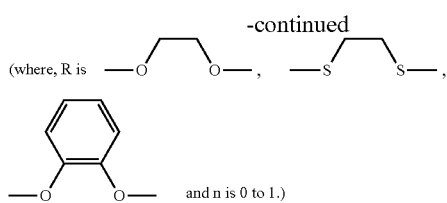 and n is 0 to 1.)

Also, a method of preparing the fluorescent sensitive compound, which is carried out according to the following scheme 3 when R is diamine, for examples,

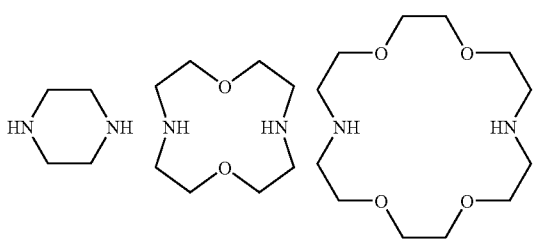

and n is 0 to 1. More specifically, the method for preparation comprises the following steps:

(1) adding an organic solution in which a 2-chloro-N-pyren-1-ylacetamide or 2-chloro-N-pyren-1-ylmethylacetamide compound (5) is contained at an equivalent ratio of 2.2 to 2.5 relative to the diamine (4) (piperazine, 1,7-dioxa-4,10-diazacyclododecane, or 1,4,10,13-tetraoxa-7,16-diazacyclooctadecane) to prepare a reaction solution and (2) reacting the resultant solution at refluxing acetonitrile or tetrahydrofuran in the presence of potassium carbonate and potassium iodide.

Furthermore, the method of preparing the fluorescent sensitive compound of the present invention further comprises, after the reaction of the step (2) in schemes 2 and 3, respectively, washing the reacted solution with water and dichloromethane as an organic solvent to obtain an organic phase; removing the solvent from the organic phase; and performing re-crystallization with a solvent combination of dichloromethane and methanol.

In the step (1), the oxalyl chloride is added in the organic solution at an equivalent ratio of 3 to 5 relative to the dicarboxylic acid (3).

Also, the organic solution in steps (1) and (2) is produced by dissolving in a polar hydrophobic organic solvent.

BRIEF DESCRIPTION OF THE DRAWINGS

The above and other objects, features and advantages of the present invention will be apparent from the following detailed description of the preferred embodiments of the invention in conjunction with the accompanying drawings, in which.

Scheme 3

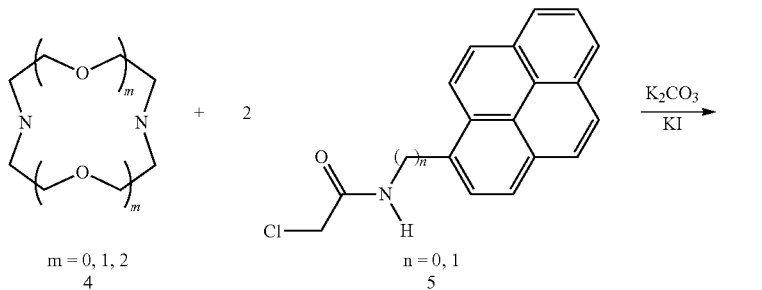

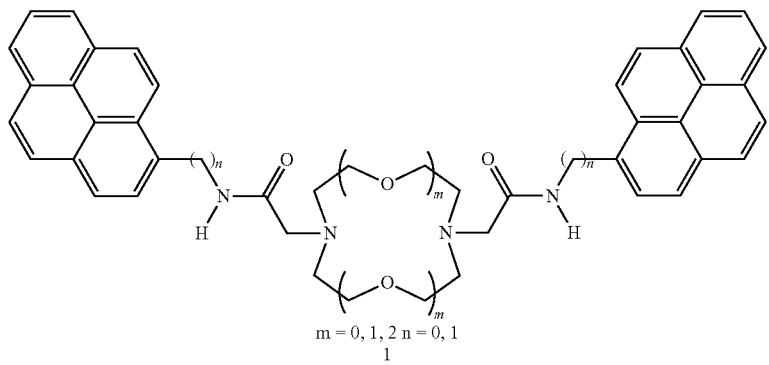

DETAILED DESCRIPTION OF THE PRESENT INVENTION

Hereinafter, the present invention is described in detail.

The present invention provides a mercury selective fluorescent chemosensor for selectively detecting mercury ions ($Hg^{2+}$) by the compound represented by the formula 1.

Formula 1

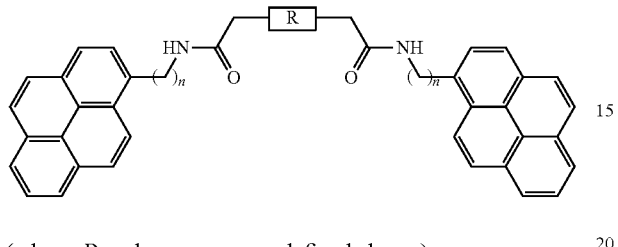

(where, R and n are same as defined above.)

A preferable example of the compound represented by formula 1, which is used in the mercury selective fluorescent chemosensor of the present invention, is a pyrene compound of 3,6-dioxaoctanediamide represented by formula 2 or a methylpyrene compound of 3,6-dioxaoctanediamide represented by formula 3.

Formula 2

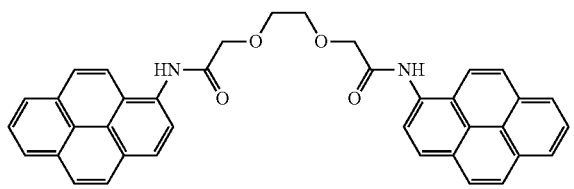

Formula 3

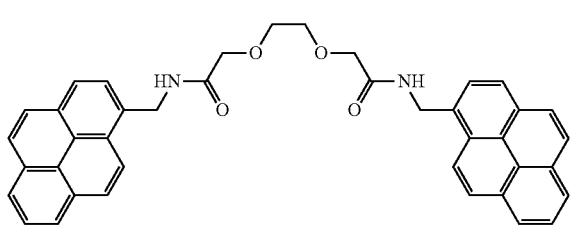

Also, other examples of the compound represented by formula 1 is any one selected from the group consisting of the compounds represented by the formula 4, formula 5, formula 6 and formula 7.

Formula 4

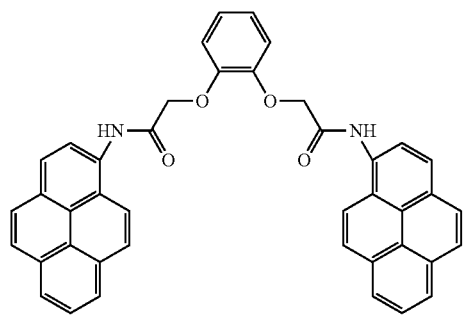

Formula 5

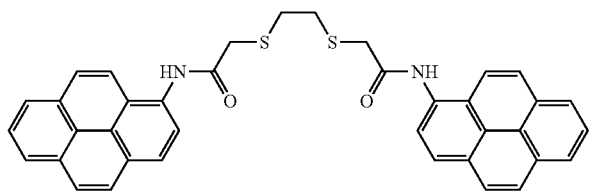

Formula 6

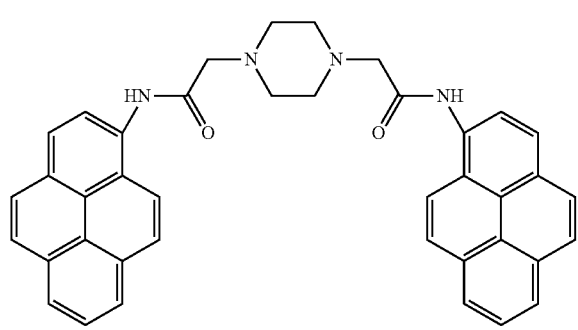

Formula 7

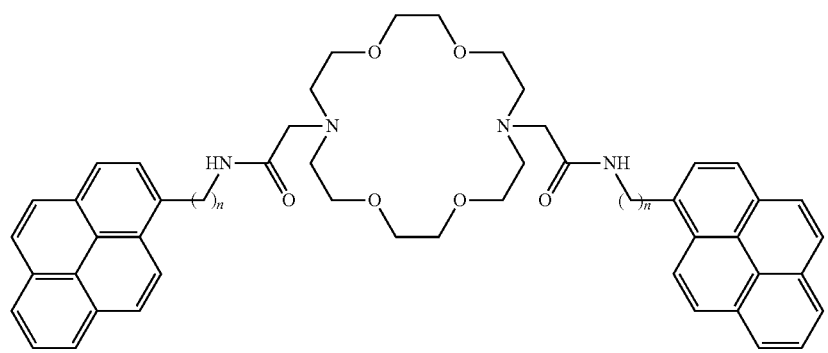

A pyrene compound of 3,6-dioxaoctanediamide represented by formula 2 is described in the Examples of the present invention, as the most preferable example of the compound represented by formula 1, but not limiting to the compound.

Figure 1:
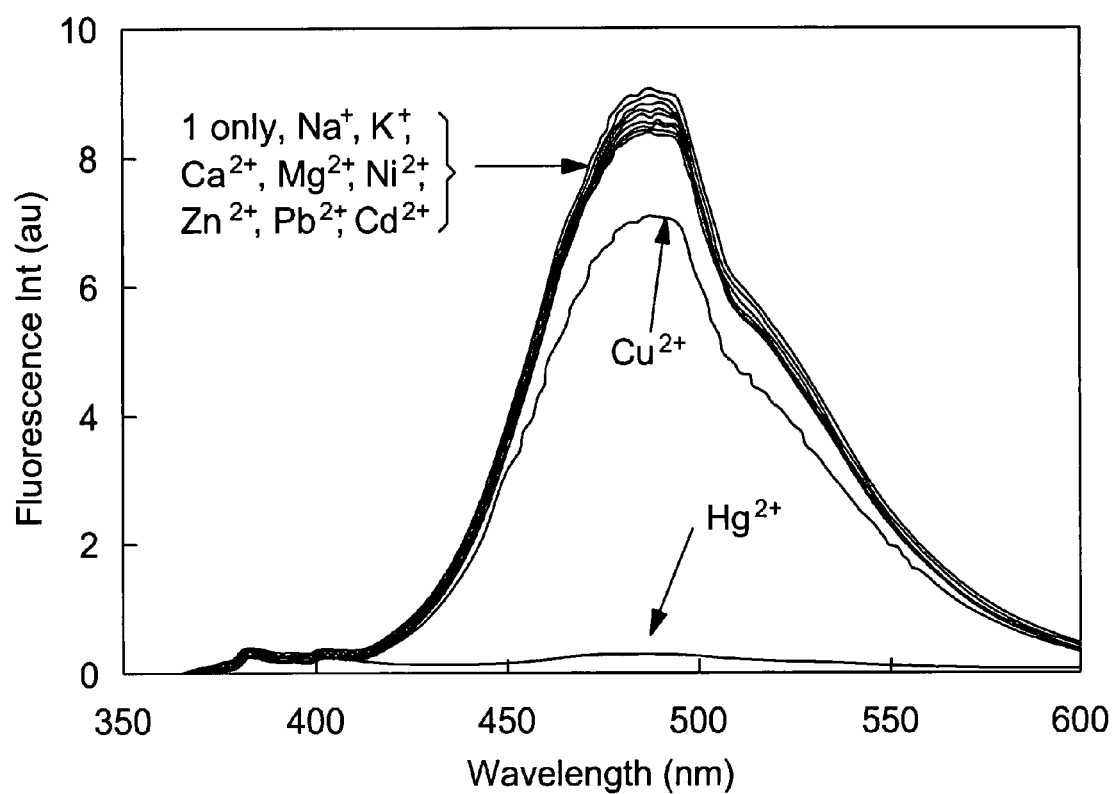
FIG. 1 is a fluorescence spectrum of the compound represented by formula 2 depending on metal ion species.

FIG. 1 represents a fluorescence spectrum of the compound represented by the formula 2 depending on metal ion species, for example, at 100 times concentration of transition metals ($Ni^{2+}$, $Cu^{2+}$, $Zn^{2+}$, $Cd^{2+}$, $Hg^{2+}$), alkali metals ($Na^+$, $K^+$) and alkaline earth metal ions ($Mg^{2+}$, $Ca^{2+}$). As can be seen from FIG. 1, the compound represented by formula 2 exhibits an intense excimer emission of the pyrene centered around 489 nm with characteristic, but very weak, monomer emissions around 380-410 nm. The ratio of fluorescence intensity of the excimer and monomer observed at 489 and 383 nm, respectively, was very large and equal to 24.9 in the 50% aqueous methanol solution. This observation implies that the compound exists in mainly stacked or folded conformations with the two pyrene moieties situated closely enough to yield the excimer. It is shown that fluorescence intensity of the compound represented by formula 2 in the presence of mercury ions ($Hg^{2+}$) is significantly reduced at 489 nm.

In particular, the fluorescence intensity ratios for the excimer and monomer emissions of the compound represented by formula 2, which were measured at 489 and 383 nm, respectively, in the absence and the presence of surveyed metal ions were almost constant (25±0.18). Only mercury ions ($Hg^{2+}$) induced a dramatic reduction (25-fold) in this ratio in the presence of 100-fold of mercury ions ($Hg^{2+}$) (see FIG. 2).

Figure 3:
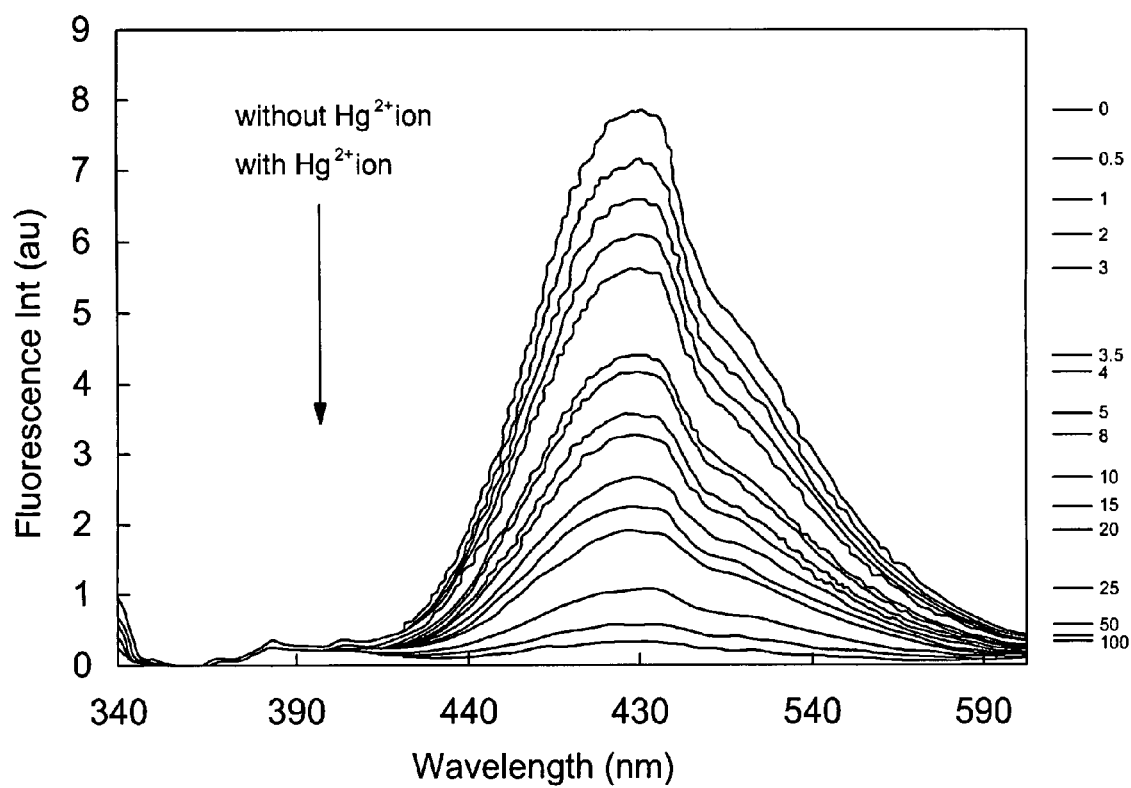
FIG. 3 is a fluorescence spectrum of the compound represented by formula 2 depending on mercury ion concentration.

Furthermore, FIG. 3 shows a fluorescence spectrum of the compound represented by formula 2 depending on mercury ion ($Hg^{2+}$) concentration. As a result, the excellent selectivity to mercury ions ($Hg^{2+}$) was exhibited under a solvent condition of methanol:water (1:1 v/v). From the result above, binding constant (Ka) and detection limit of the compound represented by formula 2 and mercury ions ($Hg^{2+}$) were estimated to be $6.2 \times 10^4$ $M^{-1}$, and $1.6 \times 10^{-6}$ M, respectively. Accordingly, the compound represented by formula 2 can detect mercury ions ($Hg^{2+}$) even to $10^{-6}$ molar concentration in a chemical or biological system.

Figure 4:
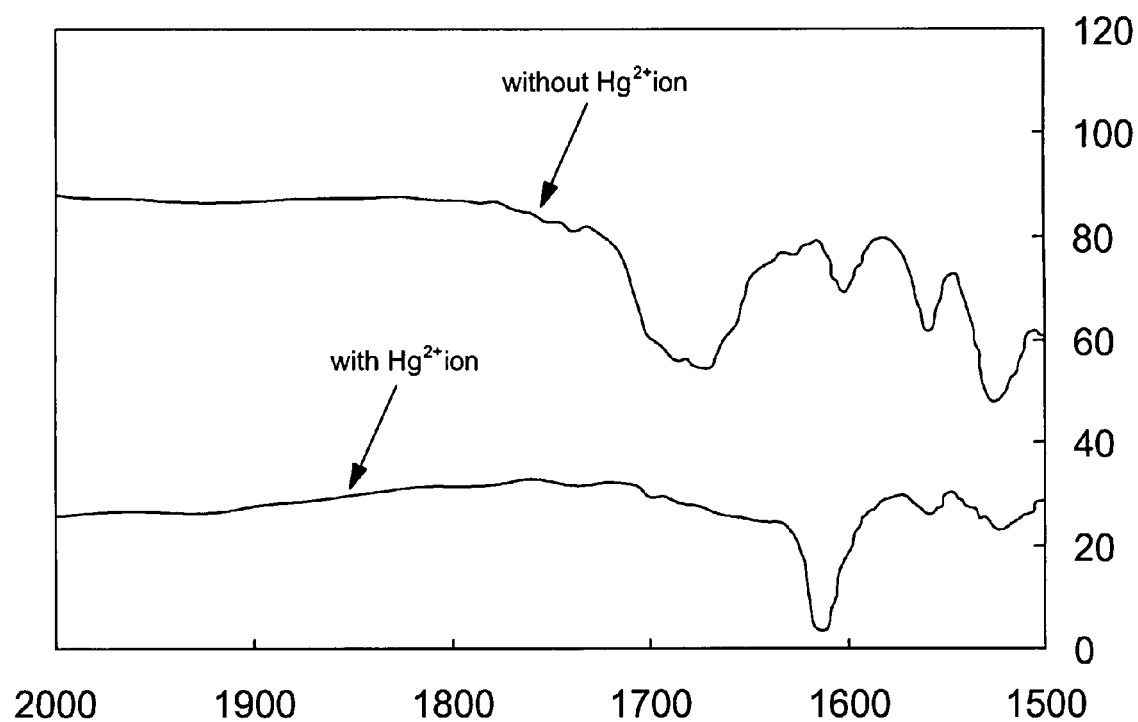
FIG. 4 is a result of IR spectrum for binding of the compound represented by formula 2 and mercury ions.
Figure 5:
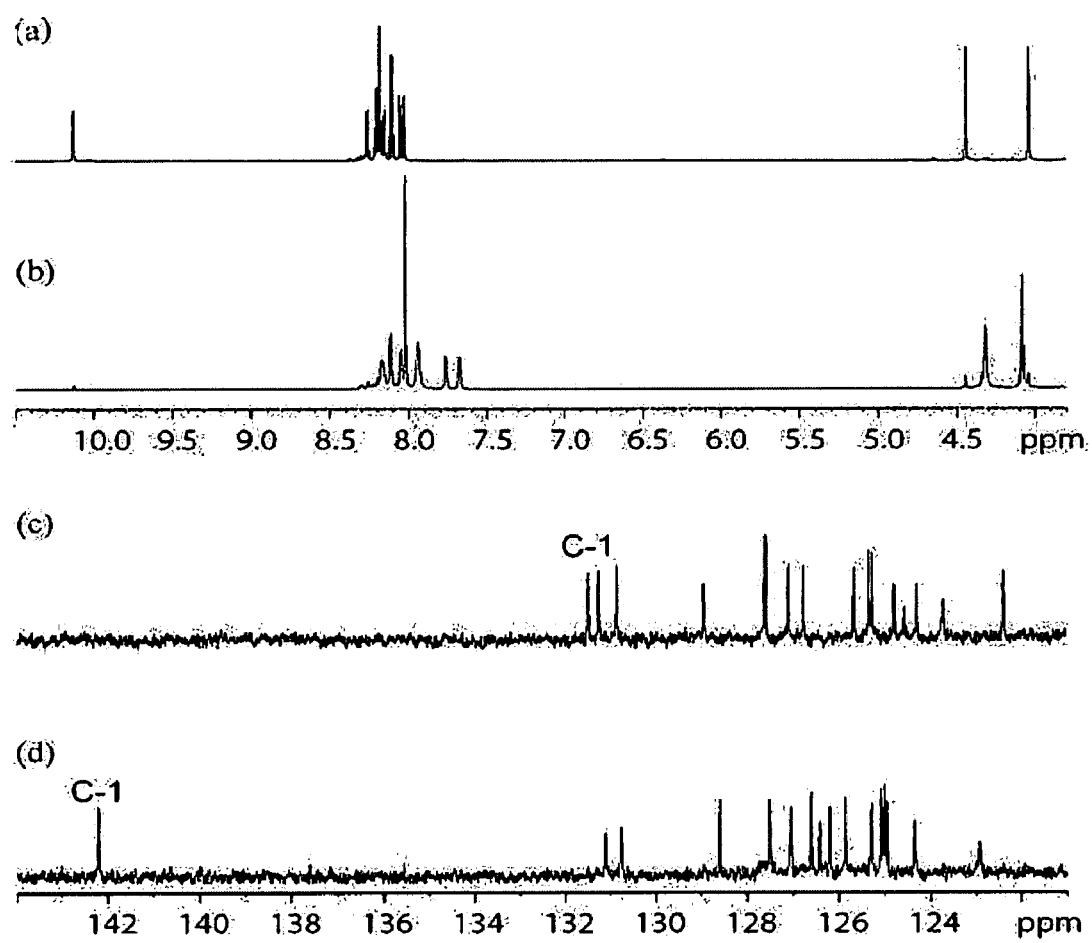
FIG. 5 is a result of NMR spectrum for binding of the compound represented by formula 2 and mercury ions.

In the present invention, a mechanism, which the compound represented by formula 1 responded selectively to mercury ions ($Hg^{2+}$), is identified by various spectroscopic experiments including FAB-MASS spectrum (not shown), IR spectrum (see FIG. 4) and NMR spectrum (FIG. 5).

As a result, the mercury selective fluorescent sensitive chemosensor of the present invention is accomplished by a fluorescence change resulting from complex formation between the compound represented by formula 2 and mercury ions ($Hg^{2+}$) (see Scheme 3). Since strong fluorescence emission due to a pyrene derivative of the compound represented by formula 2 changes to weak fluorescence emission due to the complex formation, the mercury selective fluorescent signaling characteristics of the chemosensor can be analyzed with fluorescence spectrophotometer.

Scheme 1

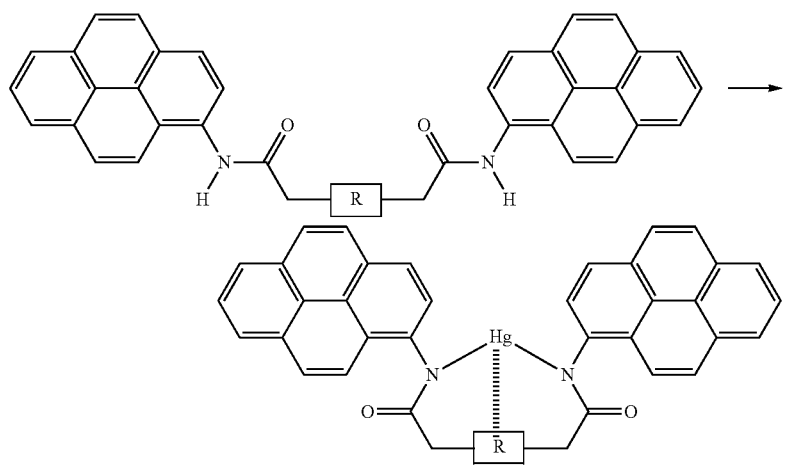

Figure 6:
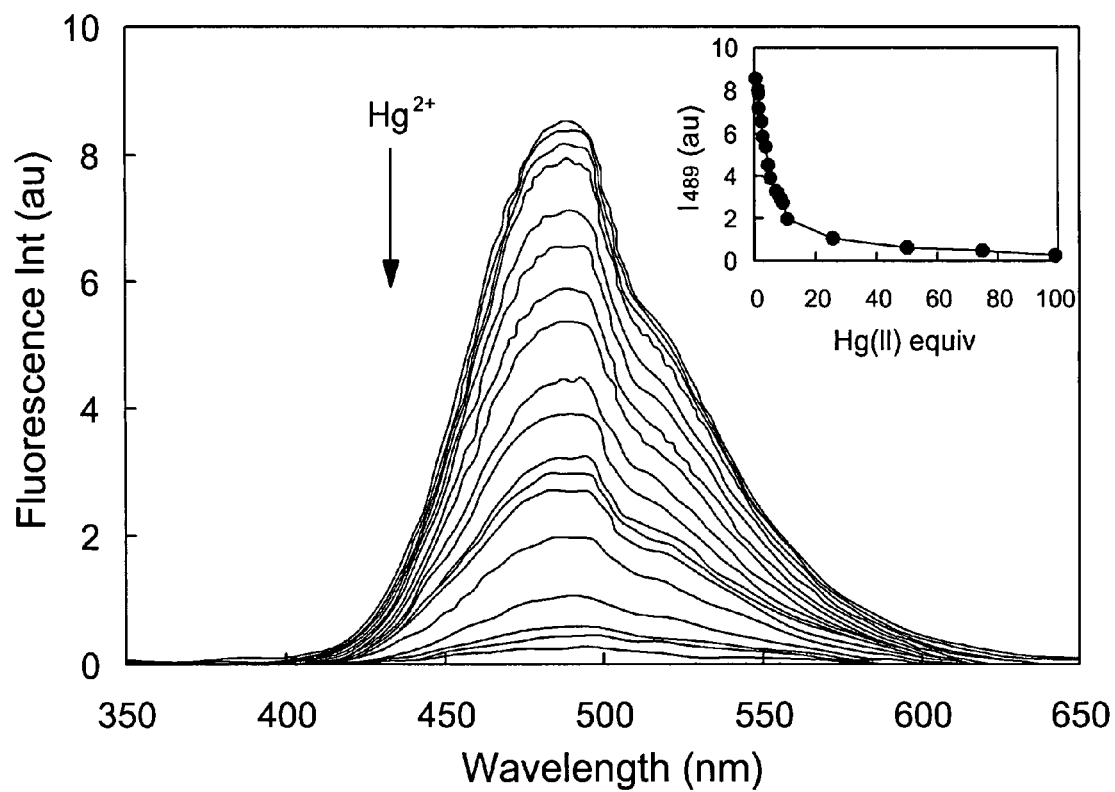
FIG. 6 is a result of performance test for the compound of the present invention as a detection sensor for detecting mercury ions ($Hg^{2+}$).

FIG. 6 represents a result of practical applicability of the compound represented by formula 2 for the analysis of mercury ions ($Hg^{2+}$). As shown in the results, the compound represented by formula 1 is not affected in detection of mercury ions ($Hg^{2+}$) in terms of sensitivity or detection limit even under the environment in which a large amount of physiologically important metal ions are present, and is detected within 5 minutes from the sample preparation time.

The mercury selective fluorescent sensitive chemosensor of the present invention shows ON-OFF-type $Hg^{2+}$-selective fluorescence quenching behavior under a solvent condition of methanol:water having a high water content, preferably under a solvent condition having a mixing ratio (1:1 to 2) of methanol:water.

Furthermore, the present invention provides fluorescent sensitive compounds represented by the formula 1 and a preparation method thereof.

Formula 1

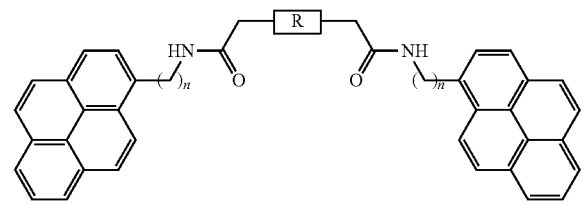

(where, R and n are the same as defined above).

More specifically, when R is

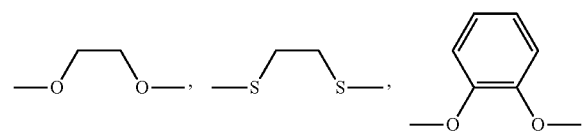

and n is 0 to 1, the method of preparing the fluorescent sensitive compound of the present invention is carried out according to the following scheme 2, and comprises the following steps:

(1) adding appropriate dicarboxylic acid (3) into an organic solution containing oxalyl chloride (($COCl)_2$) to prepare a reaction solution; and (2) adding an organic solution which contains an aminopyrene compound (2) at an equivalent ratio of 2.2 to 2.5 relative to the dicarboxylic acid (3), into the reaction solution, and then reacting the resultant solution at an ambient temperature.

Scheme 2

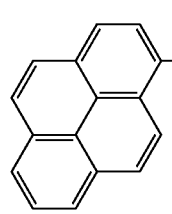

2

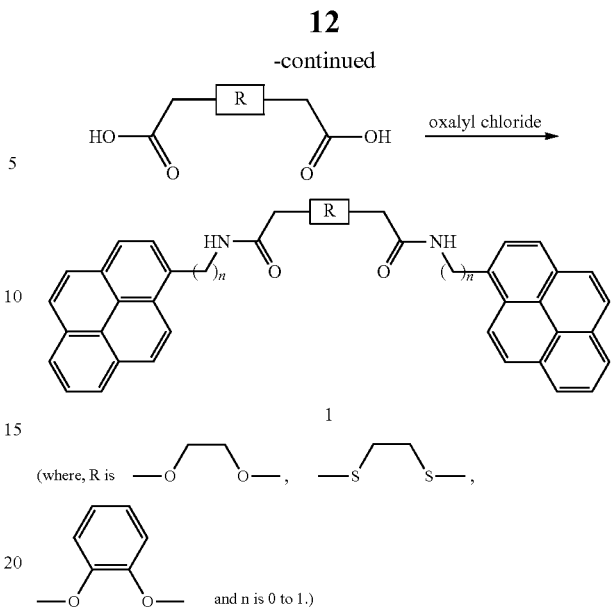

1

(where, R is

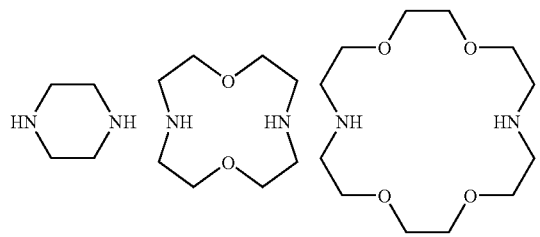

and n is 0 to 1.)

When R is diamine, for example,

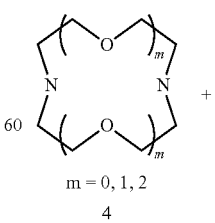

and n is 0 to 1, a method of preparing the fluorescent sensitive compound, which is carried out according to the following scheme 3; More specifically, the method for preparation comprises the following steps:

(1) adding an organic solution in which a 2-chloro-N-pyren-1-ylacetamide or 2-chloro-N-pyren-1-ylmethylacetamide compound (5) is contained at an equivalent ratio of 2.2 to 2.5 relative to the diamine (4) (piperazine, 1,7-dioxa-4,10-diazacyclododecane, or 1,4,10,13-tetraoxa-7,16-diazacyclooctadecane) to prepare a reaction solution; and (2) reacting the resultant solution at refluxing acetonitrile or tetrahydrofuran in the presence of potassium carbonate and potassium iodide.

Scheme 3

$m = 0, 1, 2$

4

-continued

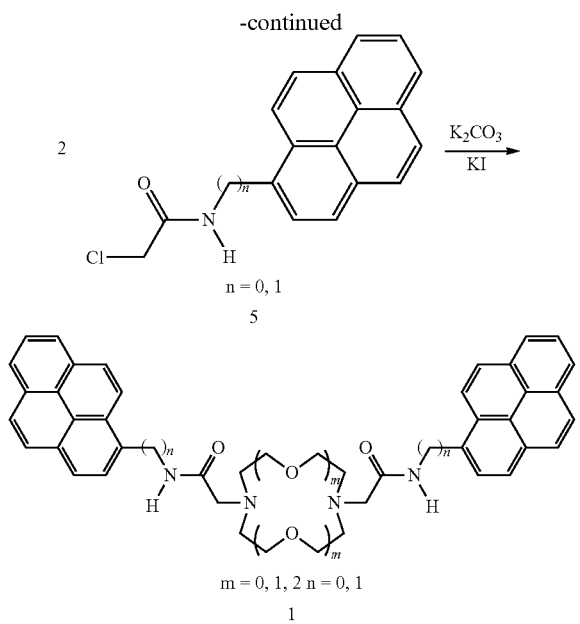

m = 0, 1, 2 n = 0, 1

1

Furthermore, after the reaction of step (2) in schemes 2 and 3, respectively, the method further comprises washing the reacted solution with water and dichloromethane as an organic solvent to obtain an organic phase; removing the solvent from the organic phase; and performing re-crystallization with a solvent combination of dichloromethane and methanol.

In the preparation method, the oxalyl chloride in the step (1) is added in the organic solution at an equivalent ratio of 3 to 5 relative to the dicarboxylic acid (3). When the equivalent ratio is less than 3, the oxalyl chloride does not convert completely into an acyl chloride form which is necessary to the reaction and thus the reaction yield becomes low. When the equivalent ratio is more than 5, it is uneconomical.

Also, step (2) is carried out by adding an organic solution containing aminopyrene compound and triethylamine (NEt$_3$) to the reaction solution and reacting them at ambient temperature. In this case, the reaction initiates upon adding and terminates within 4 hours.

The aminopyrene compound in step (2) is used at an equivalent ratio of 2.2 to 2.5 relative to the appropriate dicarboxylic acid (3). When the equivalent ratio is less than 2.2, reaction yield becomes low. When the equivalent ratio is more than 2.5, it is uneconomical.

In the preparation method, the organic solution of steps (1) and (2) is dissolved in polar hydrophobic organic solvent, and preferably halogenated hydrocarbon, more preferably dichloromethane.

Hereinafter, the present invention will be described in detail with reference to the following examples. The following examples are set forth to assist in understanding the invention and should not, of course, be construed as specifically limiting the invention described and claimed herein.

Example 1

Preparation of a pyrene compound of 3,6-dioxaoctanedioic acid 3,6-dioxaoctanedioic acid (0.28 mmol) was dispersed in 100 ml of dichloromethane (CH$_2$Cl$_2$) in which 0.1 ml of oxalyl chloride ((COCl)$_2$) and 15 µl of DMF were added, to prepare a solution. After the solution was stirred at ambient temperature for 4 hours, volatiles were removed from the solution and the residue was re-dissolved in a small amount of dichloromethane. After the solution was added slowly to dichloromethane solution in which 152 mg (0.70 mmol) of 1-aminopyrene and 0.2 ml (1.4 mmol) of triethylamine were dissolved, the solution was reacted at ambient temperature for 4 hours and the volatiles were removed. And then, the resulting product was partitioned between water and dichloromethane and the organic phase was separated and washed with water; the solvent was removed from the obtained organic phase; and then, re-crystallization was carried out with a solvent combination of dichloromethane and methanol. The target product, a pyrene compound of 3,6-dioxtanedioic acid was obtained (reddish green solid, yield: 65%).

$^1$H NMR (300 MHz, DMSO-d$_6$): δ 10.2 (s, 2H), 8.3-8.0 (m, 18H), 4.4 (s, 4H), 4.0 (s, 4H); $^{13}$C NMR (75 MHz, DMSO-d$_6$): δ 167.8, 131.1, 130.4, 128.8, 128.8, 128.0, 126.9, 126.6, 125.9, 125.4, 125.0, 124.7, 124.3, 122.4, 121.0, 118.8, 77.2, 71.4; HRMS-FAB-Mass(PEG-300/m-NBA): Calcd for C$_{40}$H$_{32}$N$_2$O$_4$ 576.2047 Found 574.2046.

Example 2

Preparation of a methyl pyrene compound of 3,6-dioxaoctanedioic acid 3,6-dioxaoctanedioic acid (0.28 mmol) was dispersed in 100 ml of dichloromethane (CH$_2$Cl$_2$) in which 0.1 ml of oxalyl chloride ((COCl)$_2$) and 15 µl of DMF were added, to form a solution. After the solution was stirred at ambient temperature for 4 hours, the volatiles were removed from the solution and re-dissolved in a small amount of dichloromethane to prepare a reaction solution. After the solution was added slowly to a dichloromethane solution in which 152 mg (0.70 mmol) of 1-aminomethylpyrene and 0.2 mL (1.4 mmol) of triethylamine were dissolved, the solution was reacted at ambient temperature for 4 hours and the volatiles were removed. And then, the resulting product was partitioned between water and dichloromethane and the organic phase was separated and washed with water; the solvent was removed from the obtained organic phase; and then, re-crystallization was carried out with a solvent combination of dichloromethane and methanol. The target product, a methyl pyrene compound of 3,6-dioxaoctanedioic acid was obtained (yellow solid, yield: 65%).

$^1$H NMR (300 MHz, DMSO-d$_6$): 8.50 (br, t, 2H), 8.4 7.9 (m, 18H), 5.0 (d, J=5.7 Hz, 4H), 4.0 (s, 4H), 3.67 (s, 4H); $^{13}$C NMR (75 MHz, DMSO-d$_6$): 169.2, 131.5, 131.4, 130.9, 129.0, 128.4, 127.8, 127.5, 126.9, 126.4, 125.7, 126.0, 125.1, 124.9, 124.8, 122.8, 70.7, 70.5, 41.0; HRMS-FAB-Mass (PEG-300/m-NBA): Calcd for C$_{38}$H$_{28}$N$_2$O$_4$ 604.2362 Found 604.2280.

Example 3

The desired product represented by formula 4 was prepared by the same method as described in Example 1, except 1,2-phenylene dioxydiacetic acid (0.28 mmol) (reddish green, yield: 65%) was used.

Example 4

The desired product represented by formula 5 was prepared by the same method as described in Example 1, except 2,2'-(ethylenedithio)diacetic acid (0.28 mmol) (ivory, yield: 63%) was used.

Example 5

Step 1: After 434.54 mg (2 mmol) of 1-aminopyrene (n=0) was dissolved in dichloromethane (50 ml), 1807.04 mg (16 mmol) of chloroacetyl chloride was added to the resulting solution to react at ambient temperature for 3 to 4 hours. After the reaction, dichloromethane solvent was removed from the solution and the residue was dissolved in a small amount of acetone. To this solution, an excess of water was added to precipitate the product 2-chloro-N-pyren-1-ylacetamide (4, n=0) which was filtered and dried.

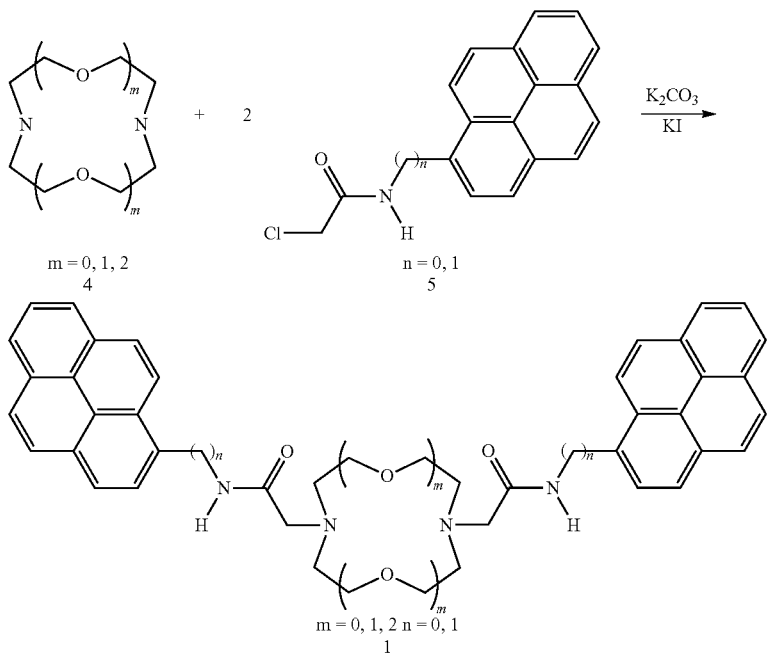

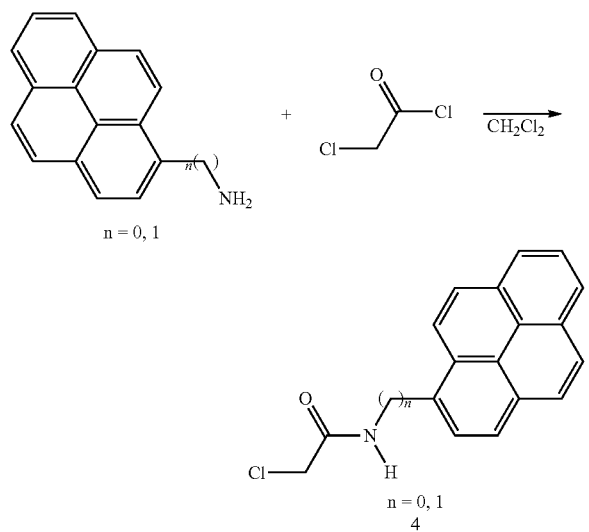

Step 2: After dissolving 1 equivalent of piperazine to 2.2 equivalents of the product obtained in the above step in acetonitrile solvent, 3 equivalents of potassium carbonate and 2 equivalents of potassium iodide were additionally added to the solution and reacted at 80° C. for approximately one day to prepare the desired product represented by the formula 1 (1, m=0, n=0) (ivory, yield: 70%).

Example 6

The desired product represented by formula 7 was prepared by the same method as described in Example 5, except 1,4,10,13-tetraoxa-7,16-diazacyclooctadecane (0.28 mmol) (ivory, yield: 70%) was used.

Experimental Example 1

Test of Fluorescence Characteristics

An ionophore characteristics of the compound represented by formula 2 produced in Example 1 was examined by determination of fluorescence. From the preliminary experiments carried out under various solvent conditions, the sensing behavior of the compound was optimized in an aqueous methanol solution and HEPES buffer (pH=7.01) for the analysis of metal ions in biological samples.

1. Change of Fluorescence Spectrum Depending on Metal Ion Species.

The fluorescence measurement of the compound represented by formula 2 was carried out in a 50% aqueous methanol solution (methanol:water=1:1, v/v). As a result, a maximum absorption band appeared at 340 nm, and typical fluorescence bands of pyrene fluorophore appeared at 383 nm and 489 nm respectively.

A fluorescence characteristics of the compound represented by formula 2 at the concentration of $5.0 \times 10^{-6}$ M was determined upon interaction with 100 equivalent of various metal ions as perchlorate salts. Metal ions, such as, transition metals ($Ni^{2+}$, $Cu^{2+}$, $Zn^{2+}$, $Cd^{2+}$, $Hg^{2+}$), alkali metals ($Na^+$, $K^+$) and alkaline earth metals ($Mg^{2+}$, $Ca^{2+}$) were used. As a result, mercury ions ($Hg^{2+}$) alone exhibited effective fluorescence quenching among the tested metal ions. The fluorescence was quenched remarkably and the intensity at 489 nm was dramatically reduced in the presence of 100 equiv of mercury ions ($Hg^{2+}$) (($I/I_0$) 0.03, where I and $I_0$ represent the fluorescence intensity in the presence and absence of metal ions, respectively). Other alkali, alkaline earth, and transition metal ions produced insignificant responses where $I/I_0$ ranged from 0.96 to 1.03 (see FIG. 1).

That is, as shown in the results of FIG. 1, when a concentration of mercury ions is $5 \times 10^{-4}$ M and a concentration of the compound represented by formula 2 is $5 \times 10^{-6}$ M, a fluorescence intensity was reduced to one forties, that is, for 100-fold concentration of mercury ions.

Figure 2:
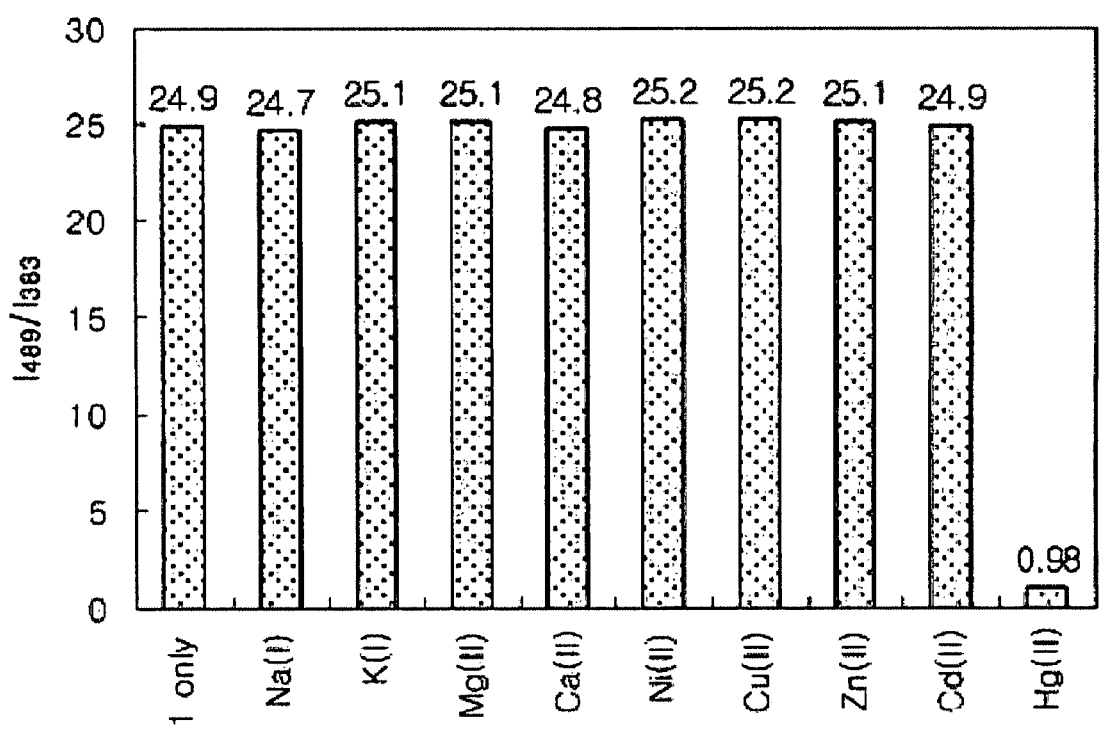
FIG. 2 is a ratiometric analysis of a monomer region and excimer region of a fluorescence spectrum of the compound represented by formula 2 depending on metal ion species.

FIG. 2 represents ratiometric plot of monomer region and excimer region of fluorescence spectrum of the compound represented by the formula 2 depending on metal ion species. As shown in FIG. 2, the fluorescence intensity ratios for the excimer and monomer emissions of the compound represented by formula 2, which were measured at 489 and 383 nm, respectively, in the absence and the presence of surveyed metal ions were almost constant (25±0.18). Only mercury ions ($Hg^{2+}$) induced a dramatic reduction (25-fold) in fluorescence intensity ratio in the presence of 100 equiv of mercury ions ($Hg^{2+}$). Accordingly, a binding between the compound represented by formula 2 and mercury ions ($Hg^{2+}$) was effective to reduce the ratio of excimer and monomer emissions of pyrene fluorophore.

As shown in the results of FIG. 1, for copper ion ($Cu^{2+}$), although the flourescence intensity was slightly reduced at a regon of 489 nm, there was no significant difference with other metal ions considereing the ratiometric relation between 383 nm and 489 nm (see FIG. 2)

2. Change of Fluorescence Spectrum Depending on the Concentration of Mercury Ions ($Hg^{2+}$)

To investigate the signaling characteristics of the compound represented by formula 2, a concentration of the compound represented by formula 2 was set to $5 \times 10^{-6}$ and excited at 340 nm, and the fluorescence spectrum was measured from 350 nm to 650 nm. In this case, fluorescence titration experiment was carried out by changing the concentration of mercury icons ($Hg^{2+}$) from 0-fold to 100 fold.

FIG. 3 represents fluorescence spectrum of the compound represented by formula 2 depending on the mercury ion concentration. As shown in the results of FIG. 3, the excellent selectivity to mercury ions ($Hg^{2+}$) was exhibited under a solvent condition of methanol:water (1:1 v/v). From the results above,
binding constant (Ka) and detection limit of the compound represented by formula 2 and mercury ions ($Hg^{2+}$) are estimated to be $6.2 \times 10^4$ $M^{-1}$ and $1.6 \times 10^{-6}$ M, respectively. Accordingly, the compound represented by the formula 2 can detect mercury ions ($Hg^{2+}$) even to $10^{-6}$ molar concentration in a chemical or biological system.

Experimental Example 2

Identification of Selectivity Toward Mercury Ions ($Hg^{2+}$)

To identify selectivity of the compound represented by formula 2 toward mercury ions ($Hg^{2+}$), the compound represented by formula 2 was reacted with mercury ions ($Hg^{2+}$) to obtain a complex, and FAB-MASS spectrum was measured for the resulting complex under a solvent condition of $CH_2Cl_2$/methanol.

The FAB-mass spectrum of the compound represented by formula 2 revealed a prominent peak at m/z=776.305, which is ascribable to a stable complex formation between the compound represented by formula 2 and mercury ions ($Hg^{2+}$). Accordingly, the mercury selective fluorescent chemosensor of the present invention is accomplished by an embodiment of the complex formation between the compound represented by formula 2 and mercury ions ($Hg^{2+}$).

IR measurements also suggest to a complex formation between the compound represented by formula 2 and mercury ions ($Hg^{2+}$).

FIG. 4 represents a result of IR spectrum for binding of the compound represented by formula 2 and mercury ions. As shown in the results of FIG. 4, an absorption band of amide carbonyl group was effectively shifted from 1678 $cm^{-1}$ to 1618 $cm^{-1}$ because of a binding of the compound represented by formula 2 and mercury ions ($Hg^{2+}$). These results supported that the carbonyl functional group is strongly participated in the complex formation between the compound represented by formula 2 and mercury ions ($Hg^{2+}$).

Furthermore, a complex formation between the compound represented by formula 2 and mercury ions ($Hg^{2+}$) was identified with $^1H$ NMR and $^{13}C$ NMR spectra.

FIG. 5 represents a result of NMR spectrum for binding of the compound represented by formula 2 and mercury ions. In FIG. 5, (a) and (c) were $^1H$ NMR and $^{13}C$ NMR spectra of the compound represented by the formula 2, and (b) and (d) were $^1H$ NMR and $^{13}C$ NMR spectra of the compound represented by formula 2 in the presence of mercury ions ($Hg^{2+}$). In this case, spectral measurements were carried out under a 20 mM concentration of DMSO-$d_6$ solvent at 320K.

The stoichiometry of the compound represented by the formula 2-$Hg^{2+}$ complex was estimated to be 1:1 by a nonlinear curve fitting of the fluorescence titration results and $^1H$ NMR titrations. As shown in the $^1H$ NMR spectra of FIG. 5, treatment of mercury ions ($Hg^{2+}$) resulted in significant shifts in the resonances of the dioxaoctanediamide backbone and pyrene moieties of the compound represented by formula 2. As a result, 4.44 ppm and 4.02 ppm peaks of methylene protons were shifted to 4.30 ppm and 4.06 ppm respectively in $^1H$ NMR spectrum with the presence of mercury ions ($Hg^{2+}$).

Particularly, a peak of pyrene carbon-1 of the compound represented by formula 2 was shifted significantly from 130.97 ppm to 141.79 ppm in $^{13}C$ NMR spectrum because of interaction with mercury ions ($Hg^{2+}$). Such significant shift suggested that amide functional groups directly linked to pyrene carbon-1 were selectively deprotonated with mercury ions ($Hg^{2+}$).

Experimental Example 3

Performance Test of Sensor for the Detection of Mercury Ions ($Hg^{2+}$)

The practical applicability of the compound represented by formula 2 for the analysis of mercury ions ($Hg^{2+}$) in the presence of a large amount of physiologically important metal ions was investigated.

The fluorescence titration of the compound represented by formula 2 with mercury ions ($Hg^{2+}$) was carried out in the presence of physiologically important metal ions as background, 138 mM of ($Na^+$), 4 mM of ($K^+$), 1 mM of ($Mg^{2+}$), 3 mM of ($Ca^{2+}$), 0.02 mM of ($Zn^{2+}$) and 0.015 mM of ($Cu^{2+}$) under a $5.0 \times 10^{-6}$ M concentration of the compound represented by the formula 2 in HEPES buffer (pH=7.01).

The resulting profile was almost identical with that obtained in the absence of any metal ions (FIG. 6). Accordingly, the compound of the present invention was not affected in detection of mercury ions (Hg$^{2+}$) in terms of sensitivity or detection limit even under the environment in which large amounts of physiologically important metal ions are present. This observation confirms that the compound represented by formula 2 of the present invention may be used as a selective ratiometric chemosensor for the analysis of Hg$^{2+}$ ions in the presence of other common competing metal ions.

As shown above, the present invention provides a mercury selective fluorescent chemosensor by a pyrene derivative based on the varying structures of diamide which are substituted at particular sites.

The chemosensor of the present invention is a switch type chemosensor having ON-OFF-type Hg$^{2+}$-selective fluorescence quenching behavior and is not affected by other metals; is used for the ratiometric analysis of micromolar mercury ions (Hg$^{2+}$) in aqueous environments even under a solvent condition having an excess amount of water.

Accordingly, the mercury selective fluorescent chemosensor for detecting mercury ions (Hg$^{2+}$) of the present invention can be used effectively in environmental and medical applications.

Also, the present invention provides a novel fluorescent sensitive compound prepared by introducing two aminopyrene functions into a binding site of variously substituted diamide and related structures and a preparation method thereof.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

Formula 1

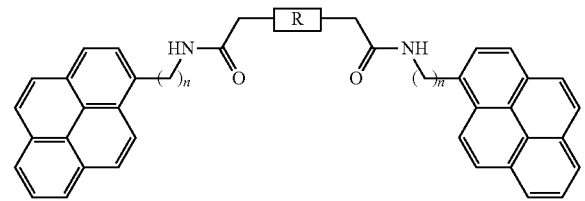

(where, R is

-continued

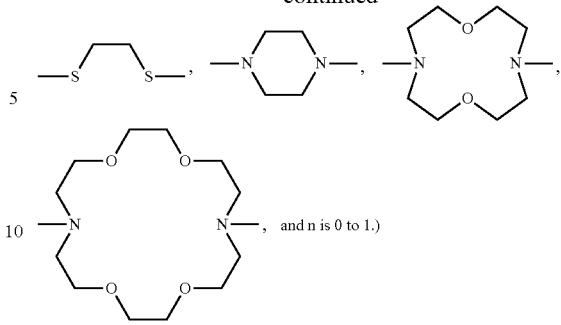

, and n is 0 to 1.)

What is claimed is:

1. A mercury selective fluorescent chemosensor having ratiometric behavior for selectively detecting mercury ions (Hg$^{2+}$) by the compound represented by the formula 1:

Formula 1

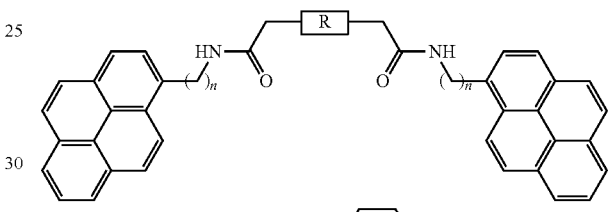

(where, R is

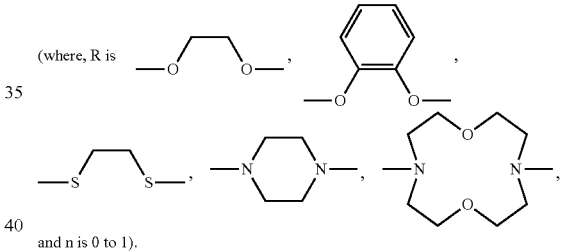

and n is 0 to 1).

2. The mercury selective fluorescent chemosensor according to claim 1, wherein the chemosensing is carried out by a fluorescence change resulting from complex formation between the compound represented by formula 1 and mercury ions (Hg$^{2+}$) according to the following Scheme 1:

Scheme 1

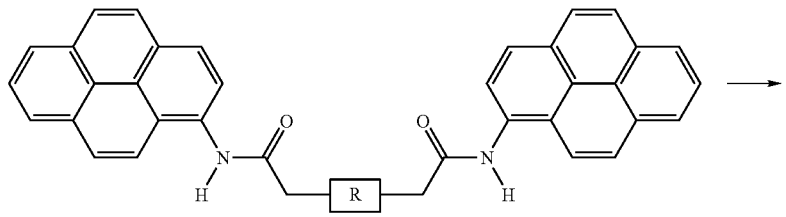

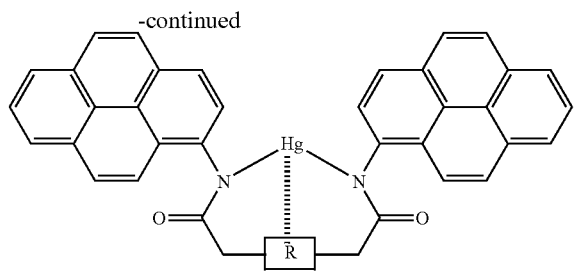

(where, R is the same as described in claim 1).

3. The mercury selective fluorescent chemosensor according to claim 1, wherein the chemosensor has ON-OFF-type $Hg^{2+}$-selective fluorescence quenching behavior under volume condition having a mixing ratio 1:1 to 2 of methanol:water.

4. The mercury selective fluorescent chemosensor according to claim 1, wherein the mercury ion ($Hg^{2+}$) is detected by a degree of $10^{-6}$ M concentration.

5. A fluorescent sensitive compound represented by formula 1:

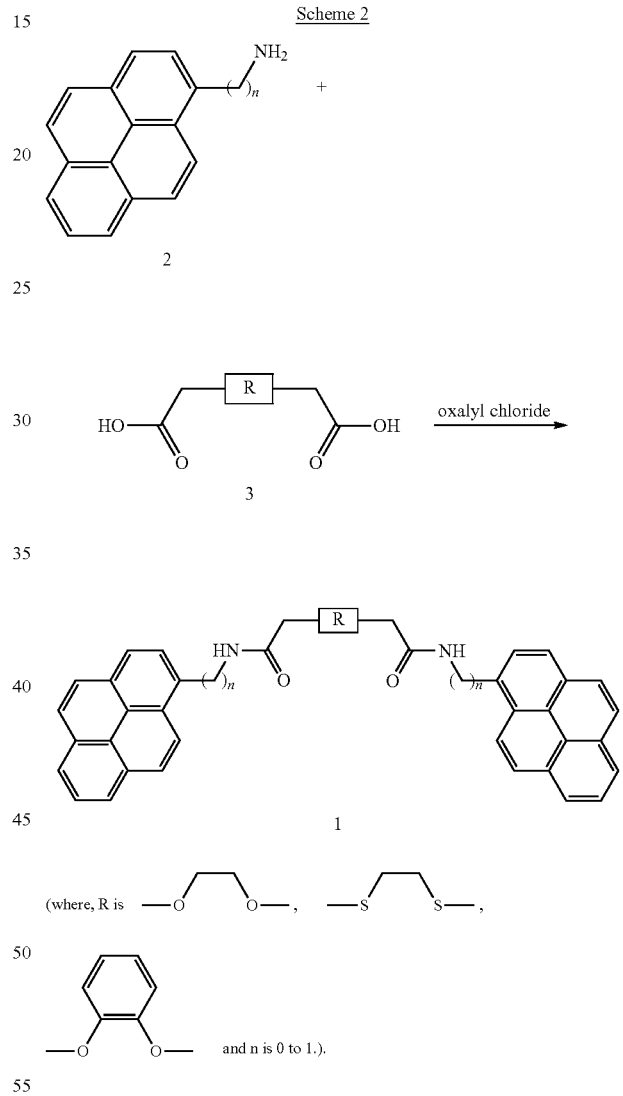

6. A method for preparing the fluorescent sensitive compound represented by the formula 1 of claim 5, comprising the following steps as shown in Scheme 2: adding dicarboxylic acid (3) into an organic solution containing oxalyl chloride ($(COCl)_2$) to prepare a reaction solution; and adding an organic solution in which an aminopyrene compound (2) is contained at an equivalent ratio of 2.2 to 2.5 relative to the dicarboxylic acid (3), into the reaction solution to form a resultant solution and then reacting the resultant solution at an ambient temperature:

7. A method for preparing the fluorescent sensitive compound represented by formula 1 of claim 5, comprising the following steps as shown in Scheme 3:

adding an organic solution in which a 2-chloro-N-pyren-1-ylacetamide compound (5) is contained at an equivalent ratio of 2.2 to 2.5 relative to the diamine (4) to prepare a reaction solution; and reacting the resultant solution at refluxing of one selected from the group consisting of acetonitrile and tetrahydrofuran in the presence of potassium carbonate and potassium iodide:

Scheme 3

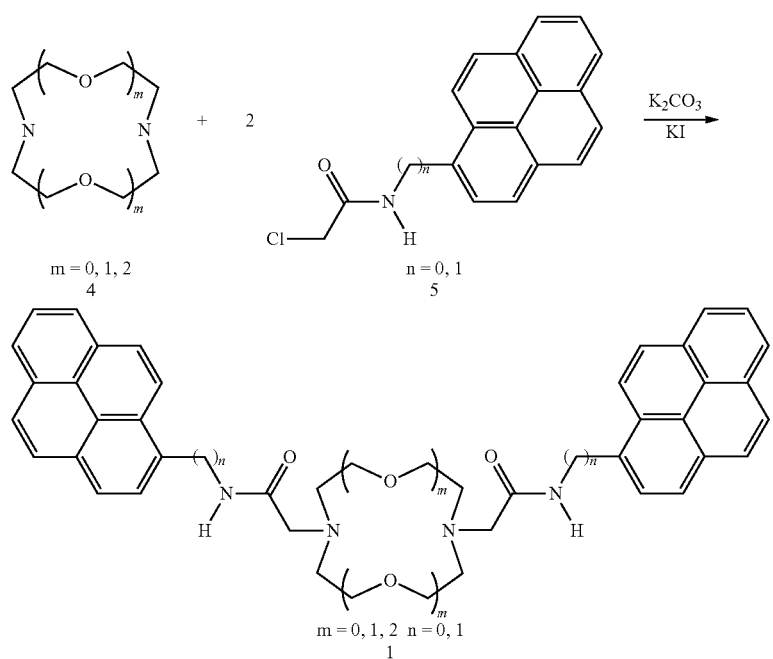

(where, m = 0, m = 1 and m = 2 represents 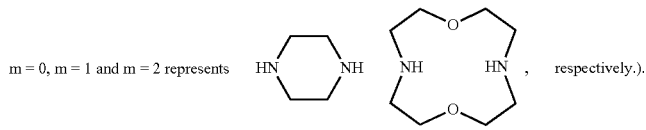 , respectively.).

8. The method according to claim 6, further comprising the steps of, after the reaction of step (2):
   washing the reacted solution with water and dichloromethane as an organic solvent to obtain an organic phase;
   removing the solvent from the organic phase; and
   performing re-crystallization with a solvent combination of dichloromethane and methanol.

9. The method according to claim 6, wherein, in step (1), the oxalyl chloride is added in the organic solution at an equivalent ratio of 3 to 5 relative to the dicarboxylic acid (3).

10. The method according to claim 6, further comprising the step of producing the organic solution in step (1) or step (2) by dissolving in a polar hydrophobic organic solvent.

11. The method according to claim 7, further comprising the steps of, after the reaction of step (2):
    washing the reacted solution with water and dichloromethane as an organic solvent to obtain an organic phase;
    removing the solvent from the organic phase; and
    performing re-crystallization with a solvent combination of dichloromethane and methanol.

12. The method according to claim 7, further comprising the step of producing the organic solution in step (1) or step (2) by dissolving in a polar hydrophobic organic solvent.

* * * * *